United States Patent [19]

Miller et al.

[11] 3,959,074

[45] May 25, 1976

[54] VACCINE PRODUCTION

[75] Inventors: William J. Miller, North Wales; Raymond E. Spier, Lansdale; William J. McAleer, Ambler, all of Pa.

[73] Assignee: Merck & Co., Inc., Rahway, N.J.

[22] Filed: Dec. 6, 1974

[21] Appl. No.: 530,109

Related U.S. Application Data

[63] Continuation of Ser. No. 262,829, June 14, 1972, abandoned, which is a continuation-in-part of Ser. No. 232,211, March 6, 1972, abandoned.

[52] U.S. Cl. .................................. 195/1.1; 424/89; 195/1.7; 195/1.8
[51] Int. Cl.² ................. A61K 39/12; A61K 39/20; C12B 1/00; C12K 7/00
[58] Field of Search ............... 195/1.7, 1.8, 1.4, 1.1; 424/89

[56] References Cited
UNITED STATES PATENTS

| | | | |
|---|---|---|---|
| 2,975,553 | 4/1961 | Paul | 195/1.8 |
| 3,407,120 | 10/1968 | Weiss et al. | 195/1.8 |
| 3,873,423 | 3/1975 | Munder et al. | 195/1.8 |

OTHER PUBLICATIONS

Hudspeth et al., Texas Reports Biology & Medicine Vol. 8 No. 3 (1950) pp. 341 & 344.

Clark et al., Applied Microbiology Vol. 19 No. 5 (1970) p. 848.

*Primary Examiner*—Sam Rosen
*Attorney, Agent, or Firm*—Donald J. Perrella; Julian S. Levitt; Harry E. Westlake, Jr.

[57] ABSTRACT

A process for the controlled manufacture of cells and vaccines in which reproducable real time quantitative assays are utilized to ascertain the physical and chemical state of the system, in order to more efficiently manage the system, so that cell sheet formation may be determined and the vaccine may be harvested at its maximum titre, thereby resulting in significantly increased yields and decreased production costs.

4 Claims, No Drawings

VACCINE PRODUCTION

This application is a streamlined continuation of U.S. Ser. No. 262,829, filed June 14, 1972, now abandoned which in turn is a continuation-in-part of U.S. Ser. No. 232,211, filed Mar. 6, 1972, now abandoned.

This invention relates to cell and vaccine production.

More particularly, this invention relates to a process for the controlled manufacture of cells and vaccines in which one or more reproducable real time quantitative assays are utilized to ascertain the physical and chemical state of the system in order to quickly and accurately determine when the maximum titre of the vaccine has been obtained. Real time assays may be defined as assays which are performed while the event system is in operation is actually occuring. For example, the point of optimum cell sheet formation can be determined during the actual cell growth phase. In addition, the maximum titre of a vaccine can be determined almost simultaneously with the point of maximum virus release from the cells as compared to conventional systems which yield this information 7 to 10 days after the event. In this way the system may be efficiently managed to avoid nonproductive or low yield runs and it can be readily determined at precisely what point to harvest and freeze the vaccine in order to obtain the highest possible yield. Additional economic advantages are realized by not having to freeze, store, process and assay lots which contain little or no virus.

Human and animal vaccines are normally produced commercially by growing the desired virus in primary cells which must be grown on surfaces. Commercial processes were initially developed in Brockway bottles and as production techniques evolved, the Brockway bottles were replaced by roller bottles. More recently, mass culture systems have been developed including those which utilize concentric rings or tanks having stacked plates.

In all of these devices it is necessary to ascertain the state of the system in order to determine the appropriate time to perform certain functions including the addition of various nitrients, the seeding of the system with the desired virus and the harvesting of the vaccine at the appropriate time. Initially, these determinations were made in a somewhat arbitrary manner, for example, the cell growth phase was allowed to proceed for a fixed period of time in all cases and no means were utilized to determine whether or not the cell growth phase had actually been completed. As production techniques evolved, experienced personnel would visually ascertain the sate of the system. However, as is readily apparent, procedures of this type have numerous disadvantages. For example such determinations are subjective, unreproducable and often arbitrary and inaccurate, and accordingly result in relatively low yields of vaccine.

The present invention provides a process for the controlled manufacture of cells and vaccines in which high yields of vaccine can be obtained at substantially decreased costs by the use of one or more reproducable real time quantitative assays which ascertain the physical and/or chemical state of the system at the time the event being monitored is actually occurring in order to efficiently manage the system to avoid non-productive or low yield runs. In this way the cell sheet can be infected at the optimum time and the vaccine can be harvested at the optimum time in order to maximize the yield.

An advantage of this invention is the production of cells and vaccines in very high yields, and at substantially reduced costs as compared to the presently utilized procedures.

A further advantage of the present invention is the ability to accurately ascertain the optimum state of a cell or vaccine production system in a quantitative manner at the time the event being monitored is actually occurring so that the production cycle and product characteristics, including the maximization of yield, may be uniformly duplicated in every production run.

A still further advantage of this invention is that optimum cell sheet formation can be readily detected during a production run, thereby greatly increasing the efficiency of the process.

Another advantage of this invention is that the time of maximum titre may be accurately determined during the production run, thereby enabling the harvesting of the vaccine at the optimum time and resulting in greatly increased yields.

The process of this invention may be used to produce viral vaccines such as mumps, measles, rubella, parainfluenza and Marek's or cells such as WI-38, chick embryo or duck embryo cells and may be carried out in devices such as Brockway bottles, roller bottles and mass cell culture systems such as concentric ring machines and multiplate propagators, as for example the unit disclosed in U.S. Pat. No. 3,407,120 or the Biotec rotating titanium disc apparatus. The most preferred device however, is a tank system such as a rotating titanium disc apparatus. Standard cells, sera and media may be used to charge the growth unit in accordance with known production techniques. For example, primary cells such as chick embryo fibroblasts, green monkey kidney, bovine kidney, dog kidney cells or diploid cells such as WI-38 may be utilized as may standard sera such as fetal calf, calf, bovine, $\alpha$-gamma calf or $\alpha$-gamma bovine and standard media such as Eagles Basel Medium, Medium 199, Medium EBME and Eagle's Minimum Essential Medium.

Included in the quantitative assays which are utilized to ascertain the physical and chemical state of the system are various assays, which monitor the chemical state of the system. For example, assays may be used which measure the level or rate of change of level of the various chemical constituents, as for example those which measure the level or rate of change of level of carbohydrates such as glucose or sucrose which are present in the system, those which measure the level or rate of change of level in the system of enzymes such as glutamic-oxalacetic transaminase and isocitric dehydrogenase and those which determine the level or rate of change of level in the system of various amino acids such as arginine, glycine, glutamine or methionine, nucleic acid derivatives such as uracil and thymine, and biochemical intermediates such as coenzymes, ATP, DPN, TPN and other intermediates which are associated with cell and vaccine production. Similarly, various assays may be performed which ascertain the physical state of the system. For example, temperature, conductivity, pH, dissolved oxygen, redox potential and various spectrophotometric effects such as absorption, fluorescence, and light scattering properties may be measured. One skilled in the art will appreciate that numerous assays may be used to monitor the chemical and physical state of the system ad that the chemical and physical criteria of different systems will vary somewhat, but the parameters of each system can be readily determined.

Commercially available equipment may be utilized to assay samples of the fluids contained in the growth unit. For example a Beckman pH probe in conjunction with a Beckman Zeromatic SS-3 meter may be utilized to quantitatively determine the pH of the fluids, a Beckman Glucose Analyzer may be utilized to determine the amount of glucose in the fluids, an Ingold Redox probe in conjunction with a Beckman Zeromatic SS-3 meter may be utilized to determine the redox potential of the fluids, a Fermentation Design dissolved oxygen probe in conjunction with a Heathkit EU-20B servorecorder may be utilized to determine the dissolved oxygen, the Sakiguchi Method may be utilized to determine the level of amino acids such as arginine, thin layer chromatography may be utilized to determine the level of amino acid derivatives and the Technicon Autoanalyzer such as the unit disclosed in U.S. Pat. No. 2,879,141, may be utilized to determine the amount of various enzymes.

As previously indicated in accordance with the present invention these assays which are performed during the production run provide data which indicates the state of the system and permits the most efficient operation of the system. For example, a typical system for the production of vaccines which employs conventional sera, media and cells, the glucose level of the fluids at the start of the cell growth cycle is in the range of 100–150 mg/100 cc. During the production cycle the glucose level is monitored in accordance with the teachings of this invention, and when this level reaches 40–60 mg/100 cc the cell growth phase is deemed to be complete for the purpose of obtaining the greatest possible efficiency in vaccine production and the desired virus seed is added. During the course of the virus growth cycle the glucose level is again monitored and should reduce to a level of 2–10 mg/100 cc in a satisfactory run. Alternatively, real time assays may be used to monitor the enzyme level in order to determine when the vaccine should be harvested at its maximum titre. For example, the vaccine should be harvested when the concentration of glutamic-oxalacetic transferase has reached its maximum rate of change or the amount of isocitric dehydrogenase has reached its maximum rate of change. As indicated previously, one or more of the various real time chemical or physical assays may be conducted in accordance with the teachings of this invention. The advantages of the instant invention as compared to the presently utilized procedures for vaccine production are readily apparent when one appreciates that these assays and determinations are performed during the production cycle as compared to the presently utilized procedures which are not performed during the production cycle and are either inaccurate approximations or require so much time as to be of little utility as production controls.

The following diagram is exemplary of typical satisfactory and unsatisfactory response curves for some of the criteria utilized in the control of cell and vaccine production in accordance with the teachings of this invention.

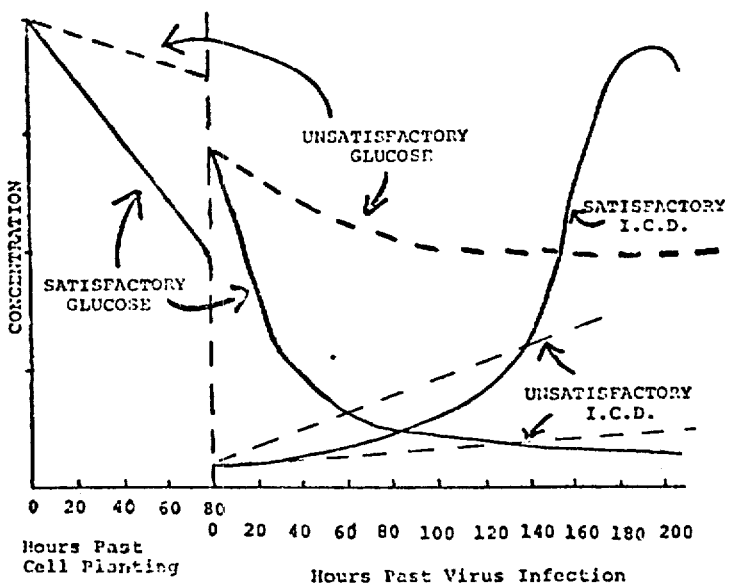

As illustrated in the above diagram, in a typical satisfactory production run the glucose level will drop from a concentration of approximately 100–150 mg/100 cc at the start of the cell growth cycle to a level of approximately 40–60 mg/100 cc at the point of optimum cell sheet formation. As shown above, in a typical unsatisfactory run, the glucose level does not decrease in this way. When a glucose level of from 40–60 mg/100 cc is reached, the virus seed is added and the decrease in glucose concentration is again monitored in accordance with the teachings of this invention. In addition, a curve depicting the concentration of isocitric dehydrogenase (ICD) in typical satisfactory and unsatisfactory runs is shown. In a satisfactory run the rate of change of the concentration increases and when the maximum rate of change is reached, the harvesting process commences. Observation of these criteria permit virus seeding and harvesting at the optimum time and enable unsatisfactory production runs to be aborted or modified as quickly as possible, thereby contributing to the overall efficiency of the production process. This is in contrast to the presently utilized procedures in which an unsatisfactory production run cannot be detected until after the run is completed or in runs in which vaccine is actually produced, the vaccine is harvested either before the maximum titre is obtained or after the titre has peaked and has begun to decrease, thereby resulting in low yields of vaccine.

A typical procedure for the production of a vaccine according to the process of this invention is described below:

EXAMPLE 1

A rotating titanium disc propagator is charged with a mixture of 1.5 billion trypsinized chick embryo cells, and Medium 199 containing 45 ml. 2.8% $NaHCO_3$/L and 10% fetal calf serum. The propagator is held in the vertical position at a temperature of 37°C. and plating is effected. The propagator is then positioned sos that the plane of the discs is in the vertical axis and a portion of the medium and serum is discharged until the unit is half full or slightly more than half full. The discs are then rotated at a speed of 1 revolution/5 minutes and air or a mixture of 95% air and 5% $CO_2$ is passed through the unit at a rate of 100 cc/minute. Samples of the supernatant fluids are taken and analyzed during the production cycle, and when the glucose concentration reaches a level of 40–60 mg/100 cc., the spent medium and serum is discharged from the propagator and the propagator is washed with Hank's solution and charged with fresh Medium 199, containing 60 ml. 2.8% $NaHCO_3$/L, and 25% SPGA containing a suspension of mumps virus derived from 0.5 ml. of a suspension which has a $-\log_{10}$ $TCID_{50}/0.1$ ml. of 3.6. The unit is again rotated at a speed of 1 revolution/5 minutes and samples of the fluid are taken and analyzed during the production cycle to determine the glutamic-oxalacetic transaminase concentration. When the rate of change of glutamicoxalacetic transaminase concentration has reached a maximum, the vaccine harvesting operation begins.

When the titre of mumps vaccine harvested according to the procedure set forth in this example is compared to that of mumps vaccine produced by conventional procedures a ten fold increase in titre is observed. This leads to a substnatial increase in yield or productivity.

EXAMPLE 2

A rotating disc propagator is charged with a mixture of 1.5 billion trypsinized chick embryo cells and Medium 199 containing 45 ml. 2.8 $NaHCO_3$/L and 10% fetal calf serum. The propagator is held in the vertical position at a temperature of 37°C. and plating is effected. After 3 hours the fluid in the propagator is discharged and a further 1.5 billion trypsinized chick embryo cells are added to it and, after mixing, the fresh suspension is transferred back into the propagator which is held in the opposite vertical position to the first plating at a temperature of 37°C. After plating has been completed the propagator is then positioned so that the plane of the discs is in the vertical axis and a portion of the medium and serum is discharged until the unit is about half full. The discs are then rotated at a speed of 1 revolution/5 minutes and a mixture of 95% air and 5% $CO_2$ is passed through the unit at a rate of 100 cc/min. Samples of the supernatant fluids are taken and analyzed during the production cycle, and when the glucose concentration reaches a level of 20–40 mg/100 cc., the spent medium and serum is discharged from the propagator, the propagator is then refed with fresh Medium 199 containing 60 ml. 2.8% $NaHCO_3$/L, and 2% α-gamma calf serum and 11 ml. of a measles virus suspension which has a $-\log_{10}$ $TCID_{50}/0.1$ ml. of 3.3. Samples of the supernatant fluids are removed periodically during the production cycle and analyzed for glucose concentration. When the glucose concentration reaches 10–30 mg/100 cc the spent fluids are discharged and the contents of the propagator are washed with Hank's solution. The propagator is then recharged with fresh Medium 199 and 60 ml. 2.8% $NaHCO_3$/L 10% SPGA. Samples of the supernatant fluids are withdrawn and analyzed for glutamic-oxalactic transaminase. When the curve describing the variation of the concentration of the enzyme glutamic-oxalacetic transaminase when time has passed through at least three minima and has reached the same value as the immediately preceding maximum the vaccine harvesting operation begins.

When the titre of measles vaccine, harvested according to the procedure set forth in this example is compared to the titre of measles vaccine produced by conventional procedures, a significant increase in titre is observed. This leads to substantially increased yields of measles vaccine.

EXAMPLE 3

A rotating disc propagator is charged with a mixture of 1.5 billion trypsinized duck embryo cells and Medium 199 containing 45 ml. 2.8% $NaHCO_3$/L and 10% fetal calf serum. The propagator is held in the vertical position at a temperature of 37°C. and plating is effected. After 3 hours the fluid in the propagator is then discharged and a further 1.5 billion trypsinized duck embryo cells are added to it and after mixing the fresh suspension is transferred back into the propagator which is held in the opposite vertical position to the first plating at a temperature of 37°C. After plating has been completed the propagator is then positioned so that the plane of the discs are in the vertical axis and a portion of the medium and serum is discharged until the unit is about half full. The discs are then rotated at a speed of 1 revolution/5 minutes and a mixture of 95% air and 5% $CO_2$ is passed through the unit at a rate of 100 cc/minute. Samples of the supernatant fluids are taken and analyzed during the production cycle, when the glucose concentration reaches a level of 20–40 mg/100 cc the spent medium and serum is discharged from the propagator, the propagator is then refed with fresh Medium 199 containing 60 ml. 2.8% $NaHCO_3$/L, 2% α-gamma calf serum and 42.7 ml. of a rubella virus suspension whose titre is $-\log_{10}$ $IND_{50}/0.1$ ml=3.5. Samples of the supernatant fluids are removed periodically during the production cycle and analyzed for glucose concentration. When the glucose concentration reaches 10–30 mg/100 ml. the spent fluids are discharged and the contents of the propagator are washed with Hank's solution. The propagator is then recharged with fresh Medium 199, 60 ml. 2.8% $NaHCO_3$/L and 10% SPGA. Samples of the supernatant fluids are withdrawn and analyzed for isocitric dehydrogenase. Thirty hours after the curve describing the variation in the level of the isocitric dehydrogenase with time has passed through its second minimum the vaccine harvesting operation begins.

When the titre of rubella vaccine, harvested according to the procedure set forth in this example, is compared to the titre of rubella vaccine derived from the conventional process, a significant increase in titre is obtained. This leads to substantially increased yields of vaccine.

EXAMPLE 4

A rotating disc propagator is charged with a mixture of 1.5 billion trypsinized chick embryo cells and Medium 199 containing 45 ml. 2.8% $NaHCO_3$/L and 10% fetal calf serum. The propagator is held in the vertical position at a temperature of 37°C. and plating is effected. After three hours the fluid in the propagator is then discharged and a further 1.5 billion trypsinized chick embryo cells are added to it and after mixing the fresh suspension, is transferred back into the propagator which is held in the opposite vertical position to the first planting at a temperature of 37°C. The propagator is then positioned so that the plane of the discs is in the vertical axis and a portion of the medium and serum is discharged until the unit is half full or slightly more than half full. The discs are then rotated at a speed of 1 revolution/5 minutes and air or a mixture of 95% air and 5% $CO_2$ is passed through the unit at a rate of 100 cc/minute. Samples of the supernatant fluids are taken and analyzed during the production cycle, and when the glucose concentration reaches a level of 40–60 mg/100 cc., the spent medium and serum is discharged from the propagator and the propagator is washed with Hank's solution and charged with fresh Medium 199, and 60 ml. 2.8% $NaHCO_3$/L, and 25% SPGA containing a suspension of mumps virus derived from 1 ml. of a suspension which has a $-\log_{10} TCID_{50}/0.1$ ml. of 3.6. The unit is again rotated at a speed of 1 revolution/5 minutes and samples of the fluid are taken and analyzed during the production cycle to determine the isocitric dehydrogenase concentration. When the rate of change of isocitric dehydrogenase concentration has reached a maximum, the vaccine harvesting operation begins.

When the titre of mumps vaccine harvested according to the procedure set forth in this example is compared to that of mumps vaccine produced by conventional procedures a ten fold increase in titre is observed. This leads to substantially increased yields of vaccine.

EXAMPLE 5

A rotating titanium disc propagator is charged with a mixture of $300 \times 10^6$ WI-38 cells in Medium EBME containing 10% fetal calf serum and 10 ml. of glutamine/L. The propagator and its contents are then held with the plane of the plates in the horizontal axis at 37°C until plating has been achieved. The propagator is then positioned so that the plane of the discs is in the vertical axis and a portion of the medium and serum is discharged until the unit is about half full. The discs are then rotated at a speed of 1 revolution/5 minutes and air or a mixture of 5% $CO_2$ and 95% air is passed through the unit at a rate of 100 cc/minute. 24 hours later the medium is discharged from the machine and the unit is refilled with an equal volume of fresh Medium EDME containing 5% fetal calf serum and 10 ml. glutamine/L. Samples of the fluids are taken and analyzed during the production cycle, and when the glucose concentration reaches a level of 5–15 mg/100 cc, the unit is harvested. For this operation the unit is voided of spent medium and is then half filled with a solution containing trypsin. The plates are then rotated through the trypsin solution at a speed of 20 revolutions per minute for 5 minutes. The cell suspension is discharged from the propagator and fetal calf serum is added until a final concentration of 7.5% fetal calf serum is obtained. The suspension is then centrifuged for 10 minutes to pellitize the cells and the cells are resuspended in Medium 199, 15% fetal calf serum and 45 ml. of 2.8% $NaHCO_3$/L.

In this way large quantities of WI-33 cells may be prepared with greater eficiency and economy when compared to cells produced by conventional procedures.

EXAMPLE 6

A rotating disc propagator is charged with a mixture of 3.0 billion trypsinized chick embryo cells, Medium 199, 45 ml. 2.8% $NaHCO_3$/L and 5% fetal calf serum. The propagator is held in the vertical position at a temperature of 37°C and plating is effected. After three hours the fluid in the propagator is discharged and a further 3.0 billion trypsinized chick embryo cells are added to it and after mixing the fresh suspension is transferred back into the propagator which is held in the opposite vertical position to the first planting at a temperature of 37°C in order to effect plating on the second side of the discs. When this has been accomplished, the propagator is positioned so that the plane of the discs is in the vertical axis and a portion of the medium and serum is discharged until the unit is about half full. The discs are then rotated at a speed of 1 revolution in 5 minutes and air or a mixture of 5% $CO_2$ and 95% air is passed through the propagator at a rate of 100 cc/min. Samples of the fluids are taken and analyzed during the production cycle, and when the glucose concentration reaches a level of 5–15 mg/100 cc the cells may be harvested.

The medium in the propagator is discharged and the propagator is filled up to the halfway mark with a solution containing trypsin. The plates are then rotated through the trypsin solution at a speed of 20 revolutions per minute for 5 minutes. The cell suspension is discharged from the propagator and fetal calf serum is added until a final concentration of 7.5% fetal calf serum is obtained. The suspension is then centrifuged for 10 minutes to pellitize the cells and the cells are resuspended in Medium 199, 15% fetal calf serum and 45 ml. of 2.8% $NaHCO_3$/L.

In this way large quantities of chick embryo cells may be prepared with greater efficiency and economy when compared to cells produced by conventional procedures.

EXAMPLE 7

A rotating disc propagator is charged with a mixture of 3.0 billion trypsinized duck embryo cells, Medium 199 F10, 5% fetal calf serum, 30 ml. 2.8% $NaHCO_3$/L. The propagator is held in the vertical position at a temperature of 37°C and plating is effected. After three hours the fluid in the propagator is discharged and a further 3.0 billion trypsinized duck embryo cells are added to it and after mixing the fresh suspension is transferred back into the propagator which is held in the opposite vertical position to the first planting at a temperature of 37°C in order to effect plating on the second side of the discs. When this has been accomplished, the propagator is positioned so that the plane of the discs is in the vertical axis and a portion of the medium and serum is discharged until the unit is about half full. The discs are then rotated at a speed of 1 revolution in 5 minutes and air or a mixture of 5% $CO_2$ and 95% air is passed through the propagator at a rate of 100 cc/min. Samples of the fluids are taken and analyzed during the production cycle, and when the glucose concentration reaches a level of 5–15 mg/100 cc the cells may be harvested.

The medium in the propagator is discharged and the propagator is filled up to the halfway mark with a solution containing trypsin. The plates are then rotated through the trypsin solution at a speed of 20 revolutions per minute for 5 minutes. The cell suspension is discharged from the propagator and fetal calf serum is added until a final concentration of 7.5% fetal calf serum is obtained. The suspension is then centrifuged for 10 minutes to pellitize the cells and the cells are resuspended in Medium 199 F10, 5% fetal calf serum, 30 ml. 2.8% $NaHCO_3$/L.

In this way large quantities of duck embryo cells may be prepared with greater efficiency and economy when compared to cells produced by conventional procedures.

What is claimed is:

1. In a process for the controlled manufacture of vaccines wherein cells are grown in a glucose containing nutrient medium and infected with a virus, isocitric dehydrogenase is released from the cells, the improvement which comprises harvesting the virus when the increase of concentration of isocitric dehydrogenase undergoes a maximum rate of change whereby production of the virus is optimized, thereby resulting in greatly increased yields and substantially decreased production costs.

2. A process according to claim 1 wherein the cells are infected with the virus when the glucose consumption after about 80 hours is at least about 40 mg/100 cc.

3. A process for the controlled manufacture of human and animal vaccines on an industrial scale whereby the production cycle is optimized, thereby resulting in greatly increased yields and substantially decreased production costs, which comprises charging a cell propagator with cells and a nutrient containing fluid in which glucose is present in a concentration of about 100–150 mg/100 cc of the nutrient medium and operating said propagator to cause growth and propagation of said cells, during operation of said cell propagator performing real time assays to monitor glucose concentration in the nutrient medium, and, when the thus monitored glucose concentration reaches about 20–60 mg/100 cc of the nutrient medium, infecting the cell sheet with a virus capable of effecting the release from said cells, isocitricdehydrogenase, maintaining conditions in said propagator to propagate said virus and, during propagation of said virus, performing real time assays to monitor said enzyme concentration in the propagator and harvesting the resulting vaccine when the monitored enzyme concentration undergoes a maximum rate of change.

4. A process as in claim 3 wherein the system is infected with the desired virus when the glucose concentration has decreased to a level of 40–60 mg/100 cc. of fluid.

* * * * *